(12) United States Patent
Dickhans

(10) Patent No.: US 11,051,886 B2
(45) Date of Patent: Jul. 6, 2021

(54) SYSTEMS AND METHODS FOR PERFORMING A SURGICAL NAVIGATION PROCEDURE

(71) Applicant: COVIDIEN LP, Mansfield, MA (US)

(72) Inventor: William J. Dickhans, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 581 days.

(21) Appl. No.: 15/277,742

(22) Filed: Sep. 27, 2016

(65) Prior Publication Data

US 2018/0085173 A1 Mar. 29, 2018

(51) Int. Cl.
*A61B 6/00* (2006.01)
*A61B 34/20* (2016.01)
(Continued)

(52) U.S. Cl.
CPC .............. *A61B 34/20* (2016.02); *A61B 6/032* (2013.01); *A61B 10/02* (2013.01); *A61B 18/1492* (2013.01); *A61B 34/25* (2016.02); *A61B 90/361* (2016.02); *A61B 90/37* (2016.02); *A61M 25/01* (2013.01); *A61B 2018/00577* (2013.01); *A61B 2034/2051* (2016.02);
(Continued)

(58) Field of Classification Search
CPC ....... A61B 34/20; A61B 90/361; A61B 90/37; A61B 34/25; A61B 6/032; A61B 10/02; A61B 18/1492; A61B 2018/00577; A61B 2090/376; A61B 2034/2057; A61B 2034/2055; A61B 2034/2051; A61M 25/01
See application file for complete search history.

(56) References Cited

U.S. PATENT DOCUMENTS 5,852,646 A 12/1998 Klotz et al.
5,930,329 A 7/1999 Navab
(Continued)

FOREIGN PATENT DOCUMENTS

CN 105658164 A 6/2016
WO 2006116749 A2 11/2006
WO 2015035287 A1 3/2015

OTHER PUBLICATIONS

Australian Examination Report issued in Appl. No. AU 2017232099 dated Feb. 19, 2018. (9 pages).
(Continued)

*Primary Examiner* — Elmer M Chao (57) ABSTRACT

A system and method for performing a navigation procedure including a surgical tool, an imaging device, and a computing device. The surgical tool is navigated to a target tissue located in a target area to perform a surgical procedure on the target tissue. The imaging device acquires image data of the target area while the surgical tool is being navigated to the target tissue by automatically traversing back and forth along a path relative to the target area and acquiring image data of the target area while traversing the path. The computing device receives the image data acquired by the imaging device and displays the image data such that the surgical tool can be navigated to the target tissue while simultaneously visualizing a position of the surgical tool relative to the target tissue from multiple perspectives relative to the target area.

15 Claims, 5 Drawing Sheets

(51) Int. Cl.

| | |
|---|---|
| *A61B 90/00* | (2016.01) |
| *A61B 34/00* | (2016.01) |
| *A61B 6/03* | (2006.01) |
| *A61B 10/02* | (2006.01) |
| *A61B 18/14* | (2006.01) |
| *A61M 25/01* | (2006.01) |
| *A61B 18/00* | (2006.01) |

(52) U.S. Cl.
CPC .............. *A61B 2034/2055* (2016.02); *A61B 2034/2057* (2016.02); *A61B 2090/376* (2016.02); *A61B 2090/3762* (2016.02)

(56) References Cited

U.S. PATENT DOCUMENTS

| | | |
|---|---|---|
| 5,963,612 A | 10/1999 | Navab |
| 5,963,613 A | 10/1999 | Navab |
| 6,038,282 A | 3/2000 | Wiesent et al. |
| 6,049,582 A | 4/2000 | Navab |
| 6,050,724 A | 4/2000 | Schmitz et al. |
| 6,055,449 A | 4/2000 | Navab |
| 6,081,577 A | 6/2000 | Webber |
| 6,120,180 A | 9/2000 | Graumann |
| 6,236,704 B1 | 5/2001 | Navab et al. |
| 6,317,621 B1 | 11/2001 | Graumann et al. |
| 6,351,513 B1 | 2/2002 | Bani-Hashemi et al. |
| 6,389,104 B1 | 5/2002 | Bani-Hashemi et al. |
| 6,404,843 B1 | 6/2002 | Valliant |
| 6,424,731 B1 | 7/2002 | Launay et al. |
| 6,484,049 B1 | 11/2002 | Seeley et al. |
| 6,485,422 B1 | 11/2002 | Mikus et al. |
| 6,490,475 B1 | 12/2002 | Seeley et al. |
| 6,491,430 B1 | 12/2002 | Seissler |
| 6,546,068 B1 | 4/2003 | Shimura |
| 6,546,279 B1 | 4/2003 | Bova et al. |
| 6,549,607 B1 | 4/2003 | Webber |
| 6,697,664 B2 | 2/2004 | Kienzle, III et al. |
| 6,707,878 B2 | 3/2004 | Claus et al. |
| 6,714,810 B2 | 3/2004 | Grzeszczuk et al. |
| 6,731,283 B1 | 5/2004 | Navab |
| 6,731,970 B2 | 5/2004 | Schlossbauer et al. |
| 6,768,784 B1 | 7/2004 | Green et al. |
| 6,782,287 B2 | 8/2004 | Grzeszczuk et al. |
| 6,785,356 B2 | 8/2004 | Grass et al. |
| 6,785,571 B2 | 8/2004 | Glossop |
| 6,801,597 B2 | 10/2004 | Webber |
| 6,823,207 B1 | 11/2004 | Jensen et al. |
| 6,856,826 B2 | 2/2005 | Seeley et al. |
| 6,856,827 B2 | 2/2005 | Seeley et al. |
| 6,865,253 B2 | 3/2005 | Blumhofer et al. |
| 6,898,263 B2 | 5/2005 | Avinash et al. |
| 6,944,260 B2 | 9/2005 | Hsieh et al. |
| 6,956,927 B2 | 10/2005 | Sukeyasu et al. |
| 7,010,080 B2 | 3/2006 | Mitschke et al. |
| 7,010,152 B2 | 3/2006 | Bojer et al. |
| 7,035,371 B2 | 4/2006 | Boese et al. |
| 7,106,825 B2 | 9/2006 | Gregerson et al. |
| 7,117,027 B2 | 10/2006 | Zheng et al. |
| 7,129,946 B2 | 10/2006 | Ditt et al. |
| 7,130,676 B2 | 10/2006 | Barrick |
| 7,165,362 B2 | 1/2007 | Jobs et al. |
| 7,251,522 B2 | 7/2007 | Essenreiter et al. |
| 7,327,872 B2 | 2/2008 | Valliant et al. |
| 7,343,195 B2 | 3/2008 | Strommer et al. |
| 7,369,641 B2 | 5/2008 | Tsubaki et al. |
| 7,440,538 B2 | 10/2008 | Tsujii |
| 7,467,007 B2 | 12/2008 | Lothert |
| 7,474,913 B2 | 1/2009 | Durlak |
| 7,502,503 B2 | 3/2009 | Bojer et al. |
| 7,505,549 B2 | 3/2009 | Ohishi et al. |
| 7,508,388 B2 | 3/2009 | Barfuss et al. |
| 7,603,155 B2 | 10/2009 | Jensen |
| 7,620,223 B2 | 11/2009 | Xu et al. |
| 7,639,866 B2 | 12/2009 | Pomero et al. |
| 7,664,542 B2 | 2/2010 | Boese et al. |
| 7,689,019 B2 | 3/2010 | Boese et al. |
| 7,689,042 B2 | 3/2010 | Brunner et al. |
| 7,693,263 B2 | 4/2010 | Bouvier et al. |
| 7,711,082 B2 | 5/2010 | Fujimoto et al. |
| 7,711,083 B2 | 5/2010 | Heigl et al. |
| 7,711,409 B2 | 5/2010 | Keppel et al. |
| 7,720,520 B2 | 5/2010 | Willis |
| 7,725,165 B2 | 5/2010 | Chen et al. |
| 7,734,329 B2 | 6/2010 | Boese et al. |
| 7,742,557 B2 | 6/2010 | Brunner et al. |
| 7,761,135 B2 | 7/2010 | Pfister et al. |
| 7,778,685 B2 | 8/2010 | Evron et al. |
| 7,787,932 B2 | 8/2010 | Vilsmeier et al. |
| 7,804,991 B2 | 9/2010 | Abovitz et al. |
| 7,831,096 B2 | 11/2010 | Williamson, Jr. |
| 7,835,779 B2 | 11/2010 | Anderson et al. |
| 7,853,061 B2 | 12/2010 | Gorges et al. |
| 7,877,132 B2 | 1/2011 | Rongen et al. |
| 7,899,226 B2 | 3/2011 | Pescatore et al. |
| 7,907,989 B2 | 3/2011 | Borgert et al. |
| 7,912,180 B2 | 3/2011 | Zou et al. |
| 7,912,262 B2 | 3/2011 | Timmer et al. |
| 7,949,088 B2 | 5/2011 | Nishide et al. |
| 7,991,450 B2 | 8/2011 | Virtue et al. |
| 8,000,436 B2 | 8/2011 | Seppi et al. |
| 8,043,003 B2 | 10/2011 | Vogt et al. |
| 8,045,780 B2 | 10/2011 | Boese et al. |
| 8,050,739 B2 | 11/2011 | Eck et al. |
| 8,090,168 B2 | 1/2012 | Washburn et al. |
| 8,111,894 B2 | 2/2012 | Van De Haar |
| 8,111,895 B2 | 2/2012 | Spahn |
| 8,126,111 B2 | 2/2012 | Uhde et al. |
| 8,126,224 B2 | 2/2012 | Zuhars et al. |
| 8,126,241 B2 | 2/2012 | Zarkh et al. |
| 8,150,131 B2 | 4/2012 | Rarer et al. |
| 8,180,132 B2 | 5/2012 | Gorges et al. |
| 8,195,271 B2 | 6/2012 | Rahn |
| 8,200,316 B2 | 6/2012 | Keppel et al. |
| 8,208,708 B2 | 6/2012 | Homan et al. |
| 8,229,061 B2 | 7/2012 | Hanke et al. |
| 8,248,413 B2 | 8/2012 | Gattani et al. |
| 8,270,691 B2 | 9/2012 | Xu et al. |
| 8,271,068 B2 | 9/2012 | Khamene et al. |
| 8,275,448 B2 | 9/2012 | Camus et al. |
| 8,306,303 B2 | 11/2012 | Bruder et al. |
| 8,311,617 B2 | 11/2012 | Keppel et al. |
| 8,320,992 B2 | 11/2012 | Frenkel et al. |
| 8,340,379 B2 | 12/2012 | Razzaque et al. |
| 8,345,817 B2 | 1/2013 | Fuchs et al. |
| 8,374,416 B2 | 2/2013 | Gagesch et al. |
| 8,374,678 B2 | 2/2013 | Graumann |
| 8,423,117 B2 | 4/2013 | Pichon et al. |
| 8,442,618 B2 | 5/2013 | Strommer et al. |
| 8,515,527 B2 | 8/2013 | Vaillant et al. |
| 8,526,688 B2 | 9/2013 | Groszmann et al. |
| 8,526,700 B2 | 9/2013 | Isaacs |
| 8,532,258 B2 | 9/2013 | Bulitta et al. |
| 8,532,259 B2 | 9/2013 | Shedlock et al. |
| 8,548,567 B2 | 10/2013 | Maschke et al. |
| 8,625,869 B2 | 1/2014 | Harder et al. |
| 8,666,137 B2 | 3/2014 | Nielsen et al. |
| 8,670,603 B2 | 3/2014 | Tolkowsky et al. |
| 8,675,996 B2 | 3/2014 | Liao et al. |
| 8,693,622 B2 | 4/2014 | Graumann et al. |
| 8,693,756 B2 | 4/2014 | Tolkowsky et al. |
| 8,694,075 B2 | 4/2014 | Groszmann et al. |
| 8,706,186 B2 | 4/2014 | Fichtinger et al. |
| 8,712,129 B2 | 4/2014 | Strommer et al. |
| 8,718,346 B2 | 5/2014 | Isaacs et al. |
| 8,750,582 B2 | 6/2014 | Boese et al. |
| 8,755,587 B2 | 6/2014 | Bender et al. |
| 8,781,064 B2 | 7/2014 | Fuchs et al. |
| 8,792,704 B2 | 7/2014 | Isaacs |
| 8,798,339 B2 | 8/2014 | Mielekamp et al. |
| 8,831,310 B2 | 9/2014 | Razzaque et al. |
| 8,855,748 B2 | 10/2014 | Keppel et al. |
| 9,001,121 B2 | 4/2015 | Finlayson et al. |
| 9,001,962 B2 | 4/2015 | Funk |

(56) References Cited

U.S. PATENT DOCUMENTS

| | | | |
|---|---|---|---|
| 9,008,367 B2 | 4/2015 | Tolkowsky et al. | |
| 9,031,188 B2 | 5/2015 | Belcher et al. | |
| 9,036,777 B2 | 5/2015 | Ohishi et al. | |
| 9,042,624 B2 | 5/2015 | Dennerlein | |
| 9,044,190 B2 | 6/2015 | Rubner et al. | |
| 9,087,404 B2 | 7/2015 | Hansis et al. | |
| 9,095,252 B2 | 8/2015 | Popovic | |
| 9,104,902 B2 | 8/2015 | Xu et al. | |
| 9,111,175 B2 | 8/2015 | Strommer et al. | |
| 9,135,706 B2 | 9/2015 | Zagorchev et al. | |
| 9,171,365 B2 | 10/2015 | Mareachen et al. | |
| 9,179,878 B2 | 11/2015 | Jeon | |
| 9,216,065 B2 | 12/2015 | Cohen et al. | |
| 9,232,924 B2 | 1/2016 | Liu et al. | |
| 9,262,830 B2 | 2/2016 | Bakker et al. | |
| 9,265,468 B2 | 2/2016 | Rai et al. | |
| 9,277,893 B2 | 3/2016 | Tsukagoshi et al. | |
| 9,280,837 B2 | 3/2016 | Grass et al. | |
| 9,282,944 B2 | 3/2016 | Fallavollita et al. | |
| 9,401,047 B2 | 7/2016 | Bogoni et al. | |
| 9,406,134 B2 | 8/2016 | Klingenbeck-Regn | |
| 9,445,772 B2 | 9/2016 | Callaghan | |
| 9,445,776 B2 | 9/2016 | Han et al. | |
| 9,466,135 B2 | 10/2016 | Koehler et al. | |
| 2001/0022834 A1* | 9/2001 | Graumann | A61B 6/4405 378/198 |
| 2001/0036245 A1* | 11/2001 | Kienzle, III | A61B 6/12 378/4 |
| 2002/0038118 A1* | 3/2002 | Shoham | A61B 17/1757 606/1 |
| 2004/0097805 A1* | 5/2004 | Verard | A61B 1/00071 600/428 |
| 2006/0058647 A1 | 3/2006 | Strommer et al. | |
| 2007/0225550 A1 | 9/2007 | Gattani et al. | |
| 2007/0268994 A1* | 11/2007 | Chen | A61B 6/032 378/4 |
| 2011/0116598 A1* | 5/2011 | Gotman | A61B 6/032 378/62 |
| 2012/0250818 A1* | 10/2012 | Helm | A61B 6/035 378/4 |
| 2013/0342578 A1* | 12/2013 | Isaacs | G06F 19/321 345/634 |
| 2015/0042643 A1 | 2/2015 | Shibata et al. | |
| 2015/0073211 A1* | 3/2015 | Dickhans | A61B 1/0014 600/104 |
| 2015/0173690 A1* | 6/2015 | Ning | A61B 90/17 600/427 |
| 2015/0196260 A1 | 7/2015 | Lee et al. | |
| 2015/0227679 A1 | 8/2015 | Kamer et al. | |
| 2015/0297311 A1 | 10/2015 | Tesar | |
| 2016/0005194 A1 | 1/2016 | Schretter et al. | |
| 2016/0120522 A1 | 5/2016 | Weingarten et al. | |
| 2016/0206380 A1 | 7/2016 | Sparks et al. | |
| 2016/0287343 A1 | 10/2016 | Eichler et al. | |

OTHER PUBLICATIONS

Extended European Search Report issued in Appl. No. EP 17193197.5 dated Jan. 26, 2018 (8 pages).

Australian Examination Report No. 2 issued in Appl. No. AU 2017232099 dated Oct. 25, 2018 (4 pages).

Canadian Office Action issued in Appl. No. CA 2,980,211 dated Aug. 31, 2018 (4 pages).

Office Action issued in corresponding Chinese Appl. No. 201710885356.1 dated Oct. 31, 2019 (10 pages).

Canadian Office Action issued in corresponding Appl. No. CA 2,980,211 dated Jul. 12, 2019 (4 pages).

Chinese Office Action issued in corresponding Appl. No. CN 201710885356.1 dated Apr. 21, 2020 (11 Pages).

* cited by examiner

SYSTEMS AND METHODS FOR PERFORMING A SURGICAL NAVIGATION PROCEDURE

BACKGROUND

1. Technical Field

The present disclosure relates to systems, methods, and devices for performing a navigation procedure, and more particularly for positioning a surgical tool using image guidance. In particular, the present disclosure relates to systems, methods, and devices for confirming proper placement of a surgical tool using imaging devices such as a fluoroscope or cone beam computed tomography device.

2. Discussion of Related Art

When planning a treatment or procedure, clinicians often rely on patient data including X-ray data, computed tomography (CT) scan data, magnetic resonance imaging (MRI) data, or other imaging data that allows the clinician to view the internal anatomy of a patient. The clinician utilizes the patient data to identify targets of interest and to develop strategies for accessing the targets of interest for the surgical procedure.

The use of CT images as a diagnostic tool has become routine and CT results are frequently the primary source of information available to a clinician regarding the size and location of a lesion, tumor, or other similar target of interest. This information is used by the clinician for planning an operative procedure such as a biopsy or an ablation procedure, but is only available as "offline" information which must typically be memorized to the best of the clinician's ability prior to beginning a procedure. During a CT scan, a patient is digitally imaged and a CT image data volume is assembled. The CT image data may then be viewed by the clinician in each of the axial, coronal, and sagittal perspectives. A clinician reviews the CT image data slice by slice from each direction when attempting to identify or locate a target. It is often difficult, however, for the clinician to effectively carry out a navigation procedure based on the previously acquired data.

SUMMARY

Systems and methods for planning and performing a surgical procedure, such as for example, a microwave ablation treatment procedure or other surgical procedure are provided. In order to navigate to a target tissue, either percutaneously using a rigid surgical tool, or via a natural orifice using a flexible extended working channel of a catheter guide assembly, a navigation plan or trajectory must be followed to get to the target tissue. Typically, the trajectory or navigation plan is determined using a workstation in a three dimensional space using previously acquired CT image data.

After a clinician navigates the surgical tool to the target, but before performing the procedure on the target, the clinician may use a fluoroscopic imaging device to confirm placement of the surgical tool relative to the target tissue. However, the fluoroscopic imaging device only provides the clinician with a two dimensional view of the surgical tool relative to the target from a single perspective. In order to gain another perspective of the placement, that is, in order to view the surgical tool relative to the target tissue from another angle, the user must move the fluoroscope relative to the target. Often, the clinician is able to see that the surgical tool is not properly positioned relative to the target tissue only upon visualizing its placement from more than one angle or perspective. Thus, what may seem to be a proper placement of the surgical tool from one perspective, may actually be an improper placement when viewed from a different perspective. After confirming that the surgical tool is not properly positioned, the clinician can move, or otherwise reposition, the surgical tool and again move the fluoroscope to view the placement from yet another angle. This process requires many iterations of moving the surgical tool and the fluoroscope before the clinician is able to confirm that the surgical tool is properly positioned.

The system and methods described herein provide solutions to the time-consuming, multi-iteration, approach of performing a navigation procedure described above. In particular, the system and methods performed by the system utilize an imaging device such as a CT, cone beam CT, or standard fluoroscope, to automatically capture a video or series or images of a target area from multiple angles relative to the target area, enabling a clinician to visualize placement of the surgical tool relative to the target tissue from multiple angles while in the process of navigating the surgical tool. This enables the clinician to correct the trajectory of the surgical tool as it progresses, without the need to retract the surgical tool to correct its placement.

One aspect provides a system for performing a navigation procedure including a surgical tool, an imaging device, and a computing device. The surgical tool is configured to be navigated to a target tissue located in a target area and to perform a surgical procedure on the target tissue. The imaging device is configured to acquire image data of the target area while the surgical tool is being navigated to the target tissue by automatically traversing back and forth along a rotational path relative to the target area and acquiring image data of the target area while traversing the path. The computing device is configured to receive the image data acquired by the imaging device and display the image data on a user interface such that the surgical tool can be navigated to the target tissue while simultaneously visualizing a position of the surgical tool relative to the target tissue from multiple perspectives relative to the target area. The user interface may be used by a clinician to set one or more parameters of the imaging device, for example, the length of the path for which the imaging device will traverse or the speed at which the imaging device traverses the path. The system may additionally include an electromagnetic field generator operably coupled to the computing device and configured to generate an electromagnetic field such that the computing device can determine a location of the surgical tool based on the electromagnetic field.

The surgical tool may include a catheter guide assembly configured to navigate to the target area via a natural orifice and the catheter guide assembly may include a handle and an extended working channel extending from the handle. A biopsy tool, a marker placement tool, a forceps, an ablation tool, or other tool may be positionable within the extended working channel to access the target tissue. Additionally, or alternatively, the surgical tool may be an ablation device including a tapered distal portion configured to percutaneously access the target tissue.

The imaging device may be configured to acquire image data which includes a plurality of fluoroscopic images where each fluoroscopic image of the plurality of fluoroscopic images is captured at a different point along the path such that each of the plurality of fluoroscopic images includes an image of the surgical tool relative to the target tissue from a different perspective. In one aspect, the imaging device may be configured to acquire image data which includes a video of the target area, such that each frame of the video includes an image of the surgical tool relative to the target tissue from a different perspective.

The imaging device may be configured to receive parameters controlling at least one of a format of the image data captured, a length of the path, or a speed at which the imaging device traverses the path. The parameters may be automatically set by the computing device or may be input by a user.

Another aspect of the present disclosure provides a method for performing a navigation procedure. The method includes initiating navigation of a surgical tool to a target tissue located in a target area and acquiring image data of the target area during navigation of the surgical tool to the target tissue by automatically traversing an imaging device back and forth along a path relative to the target area and acquiring image data of the target area while traversing the path. The method may also include displaying the acquired image data during navigation of the surgical tool to the target tissue such that a position of the surgical tool relative to the target tissue is displayed from multiple angles relative to the target area, and determining that navigation of the surgical tool to the target tissue is complete when the position of the surgical tool displayed in each of the multiple angles is at a desired location from the perspective of each of the multiple angles. The method may further include performing a procedure on the target tissue.

Initiating navigation of the surgical tool may include initiating navigation of a catheter guide assembly including an extended working channel through a natural orifice. A biopsy tool, a marker placement tool, a forceps, an ablation tool, or other tool may be positioned through the extended working channel to access the target tissue. Additionally, or alternatively, initiating navigation of the surgical tool may include percutaneously inserting an ablation tool including a tapered distal portion through tissue to access the target area.

In one aspect, acquiring image data of the target area during navigation of the surgical tool to the target tissue includes acquiring a plurality of fluoroscopic images, where each fluoroscopic image of the plurality of fluoroscopic images is captured at a different point along the path such that each of the plurality of fluoroscopic images includes an image of the surgical tool relative to the target tissue from a different perspective. Additionally, or alternatively, acquiring image data of the target area during navigation of the surgical tool to the target tissue may include acquiring a video of the target area, such that each frame of the video includes an image of the surgical tool relative to the target tissue from a different perspective.

The method may include receiving parameters controlling at least one of a format of the image data captured, a length of the path, or a speed at which the imaging device traverses the path. Additionally, or alternatively, the method may further include generating an electromagnetic field about the target area and determining a location of the surgical tool based on the electromagnetic field. In one aspect, determining that navigation of the surgical tool to the target tissue is complete includes determining that a distance between the surgical tool and the target tissue in each of the multiple angles is below a threshold.

In yet another aspect of the present disclose, a non-transitory computer-readable storage medium is provided. The non-transitory computer-readable storage medium may store instructions which, when executed by a processor, cause a computing device to acquire image data of a target area during navigation of a surgical tool to a target tissue located in the target area. The acquired image data may be received from an imaging device automatically traversing back and forth along a path relative to the target area and acquiring image data of the target area while traversing the path. The instructions, when executed, may further cause the computing device to display the acquired image data during navigation of the surgical tool to the target tissue such that a position of the surgical tool relative to the target tissue is displayed from multiple angles relative to the target area. Additionally, or alternatively, the instructions, when executed, may further cause the computing device to determine that navigation of the surgical tool to the target tissue is complete when the position of the surgical tool displayed in each of the multiple angles is at a desired position in each of the multiple angles. Additionally, or alternatively, the instructions, when executed, may further cause the computing device to determine a distance between the surgical tool and the target tissue in each of the multiple angles.

Any of the above components, aspects, and/or embodiments of the present disclosure may be combined or modified without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, of which.

DETAILED DESCRIPTION

Although the present disclosure will be described in terms of specific illustrative embodiments, it will be readily apparent to those skilled in this art that various modifications, rearrangements and substitutions of components and steps may be made without departing from the spirit of the present disclosure.

The present disclosure is directed to systems, methods, and devices for performing a navigation procedure, and more particularly for positioning a surgical tool using image guidance. For illustrative purposes only, the following detailed description and accompanying drawing figures show and detail a surgical navigation system and methods for ablation treatments. However, the claims are not limited to such ablation systems, methods and devices but rather encompasses any suitable systems, methods and devices for performing a navigation procedure.

A surgical navigation procedure for ablation treatment or other treatments, according to the present disclosure, is generally divided into two phases: (1) a planning phase, and (2) a procedure phase. The planning phase of a microwave ablation treatment is more fully described in U.S. Patent Application Publication No. 2016/0038248, entitled TREATMENT PROCEDURE PLANNING SYSTEM AND METHOD, filed on Aug. 11, 2014 by Bharadwaj et al., the entire contents of which are incorporated by reference herein.

A planning and procedure system according to the present disclosure, for example, for a microwave ablation procedure may be a unitary system configured to perform both the planning phase and the procedure phase, or the system may include separate devices and software programs for the various phases. An example of the latter may be a system wherein a first computing device with one or more specialized software programs is used during the planning phase, and a second computing device with one or more specialized software programs may import data from the first computing device to be used during the procedure phase.

Figure 1:
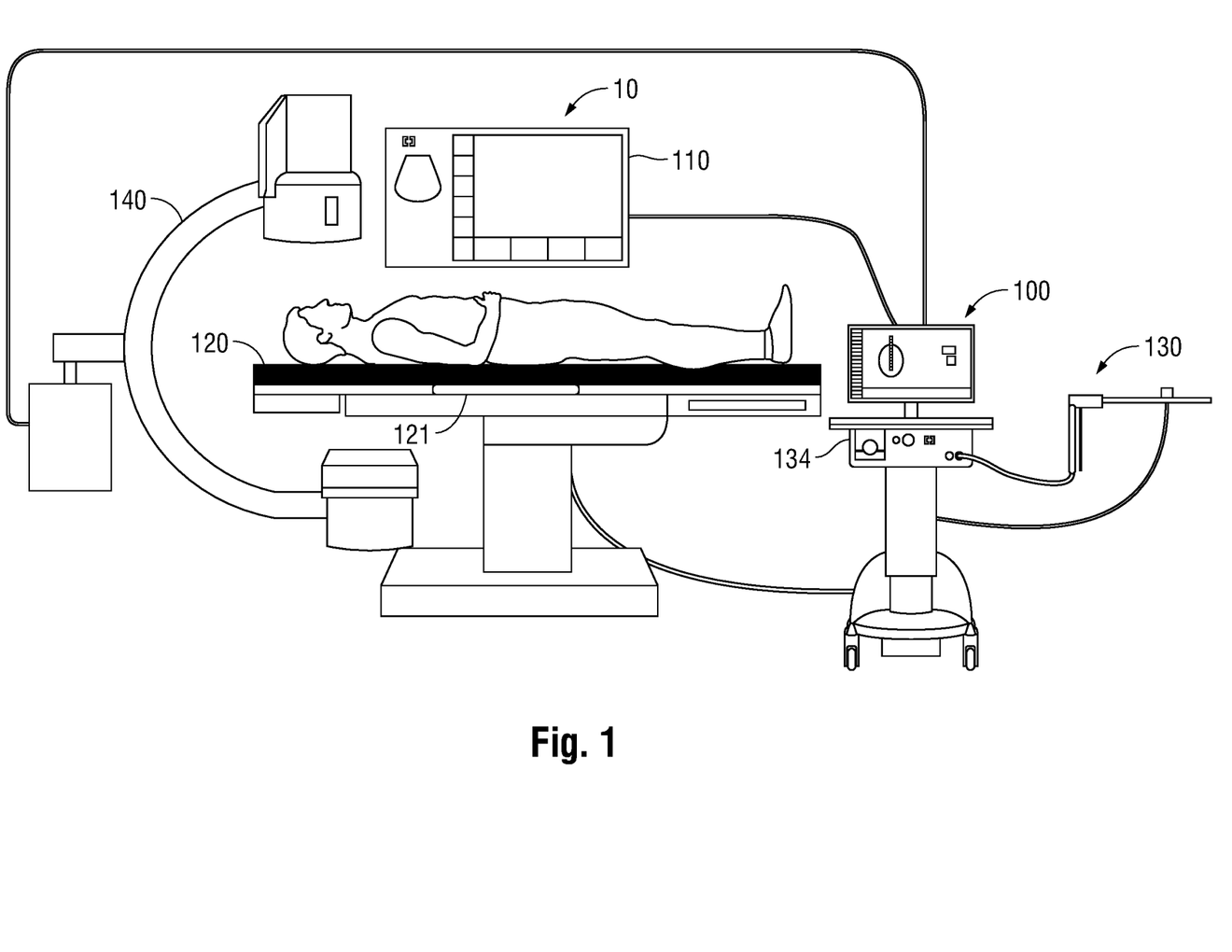
FIG. 1 is a perspective view of an illustrative embodiment of a system for performing a navigation procedure incorporating an imaging device in accordance with the present disclosure.

Referring now to FIG. 1, the present disclosure is generally directed to a procedure system 10, which may be used to navigate to a target within a patient's body and perform a procedure on the target. System 10 includes a computing device 100, a display 110, a table 120, a surgical tool 130, and an imaging device 140. Computing device 100 may be, for example, a laptop computer, desktop computer, tablet computer, or other similar device. Computing device 100 may be configured to control an electrosurgical generator, a fluid pump, a power supply, and/or any other accessories and peripheral devices relating to, or forming part of, system 10. Additionally, computing device 100 may include an electrosurgical generator 134 configured to generate electrosurgical energy such as microwave ablation energy. Display 110 is configured to display user interfaces which include parameter setting inputs, output instructions, images, messages relating to the performance of the procedure, and other useful user interfaces.

System 10 may be configured for reviewing previously acquired CT image data to identify one or more targets, planning a pathway to an identified target (planning phase), navigating a tool to a target (navigation/procedure phase) via a user interface, and confirming placement of the surgical tool 130 relative to the target. To this end, system 10 may be used to navigate surgical tools to a target through a natural orifice using an extended working channel of a catheter guide assembly 200 (FIG. 2), for example through a branched luminal network of a patient, or percutaneously using an surgical tool having a tapered distal portion, such as ablation tool 300 (FIG. 3). An example system is the ELECTROMAGNETIC NAVIGATION BRONCHOSCOPY® system, or the ILOGIC® suite, currently sold by Medtronic PLC. The target may be tissue of interest or a region of interest identified during review of the CT image data during the planning phase. The procedure performed on the target may include obtaining a tissue sample from the tissue located at or proximate to, the target, delivering items, such as radio-opaque markers and/or therapeutic agents to the region of the target, or treating the target using electrosurgical or microwave energy.

Although not explicitly shown, surgical tools 130 that may be used with system 10 include catheter guide assemblies 200 (FIG. 2) configured to navigate to targets through a natural orifice, such as those currently marketed and sold by Medtronic PLC under the brand names SUPERDIMENSION® Procedure Kits or EDGE™ Procedure Kits. For a more detailed description of these catheter guide assemblies, reference is made to commonly-owned U.S. Pat. No. 9,247,992, filed on Mar. 15, 2013, by Ladtkow et al., U.S. Pat. No. 7,233,820, filed on Apr. 16, 2003, and U.S. Pat. No. 9,044,254, filed on Mar. 15, 2013, the entire contents of each of which are incorporated by reference herein. Additionally, or alternatively, as detailed below, system 10 may be used with surgical tool 130 such as ablation tool 300 (FIG. 3) configured to percutaneously access a target tissue site and deliver ablation energy to the target tissue. Further, surgical tool 130 may include biopsy tools, chemotherapy catheters for localized treatment, balloon catheters or any other such device. To this end, surgical tool 130 may be a device used to navigate any of the above-described tools or may be the actual device itself.

Continuing with reference to FIG. 1, table 120 may be, for example, an operating table or other table suitable for use during a surgical procedure, which includes an electromagnetic field generator 121. Electromagnetic field generator 121 is used to generate an electromagnetic field during the navigation procedure and forms part of an electromagnetic tracking system which is used to track the positions of surgical instruments within the body of a patient. Electromagnetic field generator 121 may include various components, such as a specially designed pad to be placed under, or integrated into, an operating table or patient bed. An example of such an electromagnetic tracking system is the AURORA™ system sold by Northern Digital Inc.

Surgical tool 130 may be a surgical instrument having a microwave ablation antenna which is used to ablate tissue. Surgical tool 130 can used to ablate a target tissue (for example, a lesion or tumor) by using electromagnetic radiation or microwave energy to heat tissue in order to denature or kill cancerous cells. The construction and use of a system including such a surgical tool 130 is more fully described in co-pending U.S. Patent Application Publication No. 2016/0058507 entitled MICROWAVE ABLATION SYSTEM, filed on Aug. 18, 2015, by Dickhans, U.S. Pat. No. 9,247,992 entitled MICROWAVE ABLATION CATHETER AND METHOD OF UTILIZING THE SAME, filed on Mar. 15, 2013, by Ladtkow et al., and U.S. Pat. No. 9,119,650 entitled MICROWAVE ENERGY-DELIVERY DEVICE AND SYSTEM, filed on Mar. 15, 2013, by Brannan et al., the entire contents of each of which are incorporated by reference herein.

In addition to the electromagnetic tracking system, after a surgical tool 130 is navigated to a target area using a preplanned trajectory, imaging device 140 may be used to visualize the location of the surgical tool 130 relative to a target inside the patient's body. Imaging device 140 may be any device suitable for visualizing the navigated surgical tool 130 relative to the target tissue. For example, imaging device 140 may include a CT imaging device, a cone beam CT imaging device, or a fluoroscopic imaging device.

Figure 2:
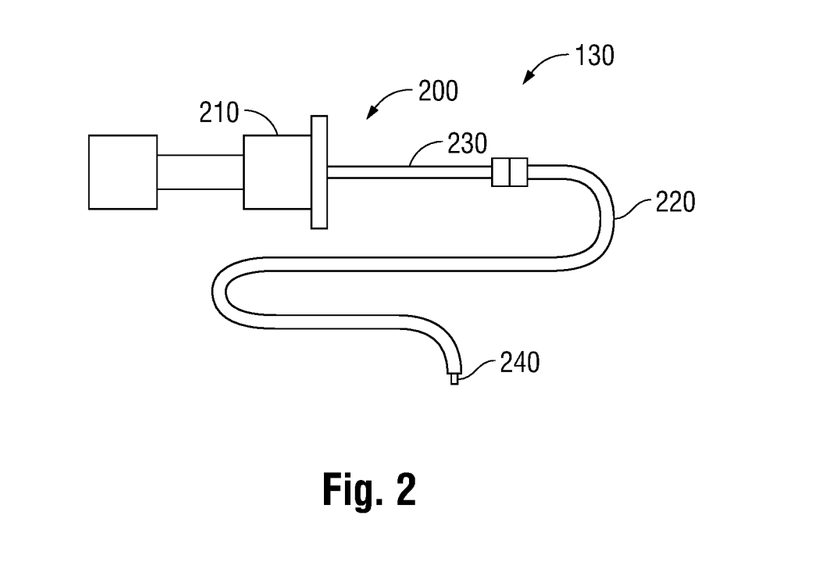
FIG. 2 is a plan view of an illustrative embodiment of a catheter guide assembly usable with the system of FIG. 1 to navigate through a natural orifice of a patient to access a target tissue.
Figure 3:
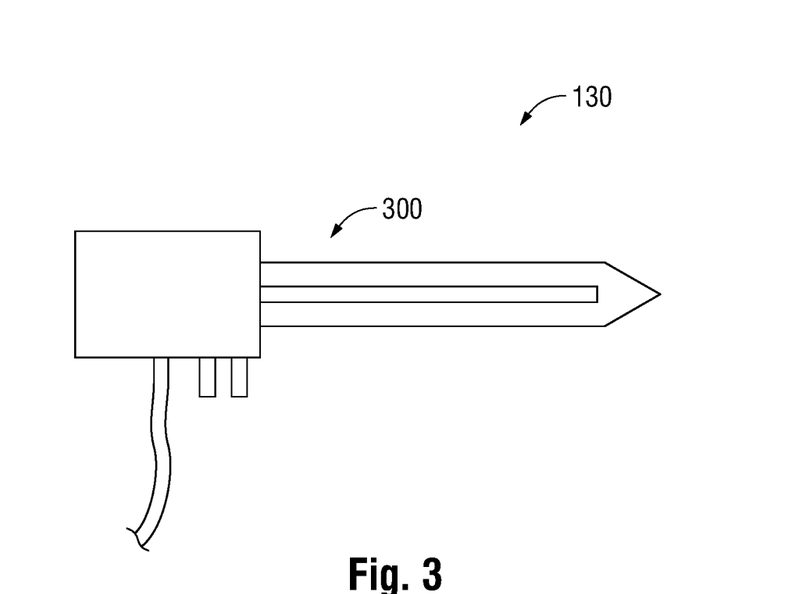
FIG. 3 is a plan view of an illustrative embodiment of an ablation device usable with the system of FIG. 1 to percutaneously access a target tissue.

FIG. 2 illustrates an example surgical tool 130 (FIG. 1) as a catheter guide assembly 200 usable with the system 10 and introducible through a natural orifice of a patient. Catheter guide assembly 200 includes a handle 210 and an extended working channel (EWC) 220 which extends distally from handle 210. In practice, the EWC 220 is inserted into a bronchoscope for access to a luminal network of the patient. Specifically, EWC 220 of catheter guide assembly 200 may be inserted into a working channel of a bronchoscope for navigation through a patient's luminal network. A locatable guide (LG) 230, including a sensor 240 disposed thereon, is inserted into the EWC 220 and locked into position such that the sensor 240 extends a desired distance beyond the distal tip of the EWC 220. In certain aspects, EWC 220 includes sensor 240 disposed thereon (for example, on the distal portion of EWC 220), eliminating the need for a separate LG 230. The position and orientation of the sensor 240 relative to a reference coordinate system, and thus the distal end of the EWC 220, within an electromagnetic field can be derived by system 10 using the electromagnetic field generator 121. As noted above, catheter guide assemblies 200 are currently marketed and sold by Medtronic PLC under the brand names SUPERDIMENSION® Procedure Kits or EDGE™ Procedure Kits, and are contemplated as useable with the present disclosure. As also described above, a more detailed description of these catheter guide assemblies, reference is made to commonly-owned U.S. Pat. No. 9,247,992, filed on Mar. 15, 2013, by Ladtkow et al., U.S. Pat. No. 7,233,820, filed on Apr. 16, 2003, and U.S. Pat. No. 9,044,254, filed on Mar. 15, 2013, the entire contents of each of which are incorporated by reference herein.

FIG. 3 illustrates an example of a surgical tool 130 (FIG. 1) as an ablation tool 300 usable with the system 10 which is used to percutaneously access a target tissue site of the patient. As described above, the construction and use of such a surgical tool 130 is more fully described in co-pending U.S. Patent Application Publication No. 2016/0058507 entitled MICROWAVE ABLATION SYSTEM, filed on Aug. 18, 2015, by Dickhans, U.S. Pat. No. 9,247,992 entitled MICROWAVE ABLATION CATHETER AND METHOD OF UTILIZING THE SAME, filed on Mar. 15, 2013, by Ladtkow et al., and U.S. Pat. No. 9,119,650 entitled MICROWAVE ENERGY-DELI VERY DEVICE AND SYSTEM, filed on Mar. 15, 2013, by Brannan et al., the entire contents of each of which are incorporated by reference herein.

Figure 4:
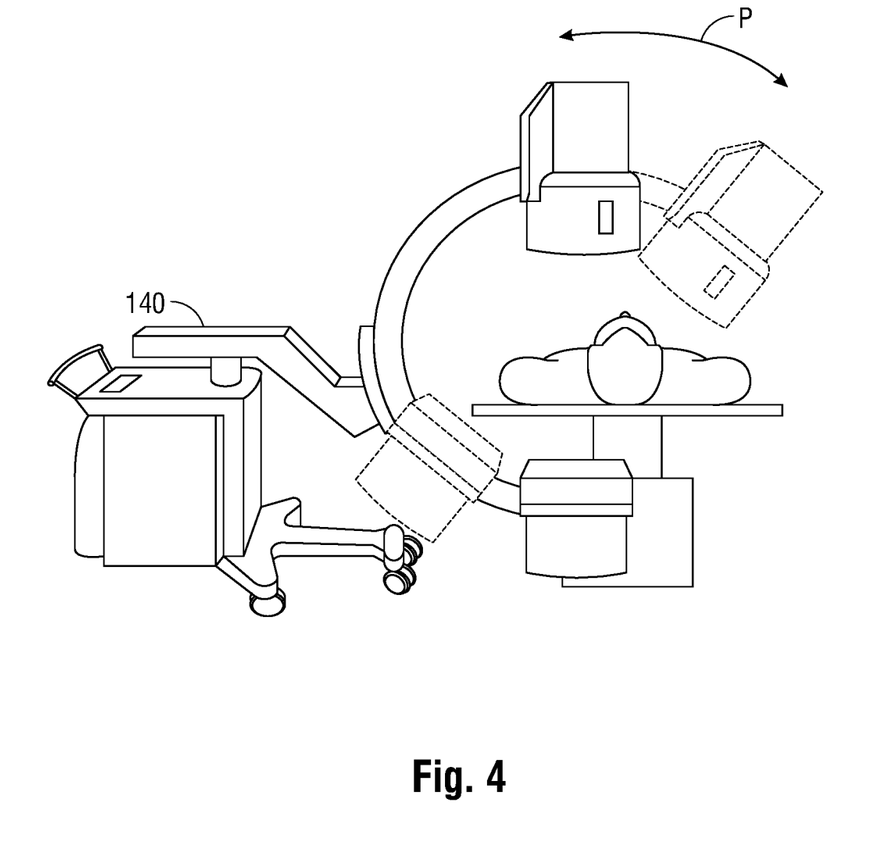
FIG. 4 is an illustration of an imaging device traversing a path relative to a patient.

Turning now to FIG. 4, an imaging device 140 (also referred to herein as a "CT imaging device 140") is shown in a position relative to the patient during or after navigation of a surgical tool 130 (either catheter guide assembly 200 of FIG. 2 or ablation tool 300 of FIG. 3) to a desired target tissue site. The CT imaging device 140 moves along path "P" while capturing image data (for example, a video or a series of images) along path "P" from different perspectives relative to the patient or target area. In particular, CT imaging device 140 slowly reciprocates back and forth along path "P" and transmits the acquired image data to computing device 100 for processing and/or display of the image data on display 110. In one aspect, CT imaging device 140 includes a C-arm and a motor for moving an imager of the CT imaging device 140 along the C-arm.

The image data may include fluoroscopic images, fluoroscopic video, or other CT data. Computing device 100 displays the acquired CT data on display 110 such that a clinician can visualize the position of the surgical tool 130 relative to the target tissue from multiple perspectives, without the need to iteratively adjust the position of the CT imaging device 140, and readjust the position of the surgical tool 130 multiple times before reaching the desired target tissue. In particular, computing device 100 provides the clinician with a continuous multi-perspective or multi-angle visualization of the target region, thereby enabling the clinician to interpolate the three-dimensional space and simultaneously navigate the surgical tool 130 to the target tissue without being required to repeatedly retract the surgical tool 130 and correct its trajectory.

The length of path "P" to which imaging device 140 traverses may be selected or modified by computing device 100 or may be selected or modified by a clinician. In particular, a clinician may choose the length of the path "P" for which the imaging device 140 will traverse along in order to suit the particular needs of the navigation procedure. The length of path "P" is directly correlated to the range of angular positions of the imaging device 140 relative to the patient. In some instances it may be useful for the clinician to visualize the target area from a large range of perspectives (greater angular range) and in some other instances it may be useful for a clinician to visualize the target area from a small range of perspectives (lower angular range).

Additionally, the speed at which the imaging device 140 traverses the path "P" may also be selected or modified by the computing device 100 or the clinician. In particular, a clinician may choose the speed at which the imaging device 140 traverses along the path "P" in order to suit the particular needs of the navigation procedure. That is, in some instances it may be useful for the clinician to visualize the target area while receiving images or video of the target area while the imaging device 140 traverses back and forth along path "P" at a fast speed and in some other instances it may be useful for the clinician to visualize the target area while receiving images or video of the target area while the imaging device 140 traverses back and forth along path "P" at a slow speed. The faster the imaging device 140 traverses along the path "P," the faster the images and/or video captured by the imaging device 140 are displayed to the user. At certain higher speeds, the user may visualize the two-dimensional object in the two-dimensional frames and/or video as a three-dimensional-like object. Thus, when the display 110 displays the movement around the object (for example, the target), the user may interpolate the three-dimensional space and thus understand the multiple two-dimensional perspectives of the object as a three-dimensional-like object.

Additionally, the type or format of the image data acquired by the imaging device 140 may be selected or modified by the computing device 100 or may be selected or modified by a clinician. In particular, in certain instances it may be beneficial to receive the image data as a video stream to maximize the visualization of the target area. In other instances it may be useful for the image data to be a series of images taken along the path "P." For example, in instances where a clinician may desire to expose the patient to lower amounts of radiation, the clinician may select the image data to be a series of images, or a combination of a series of images and video along different portions of the path "P."

Figure 5:
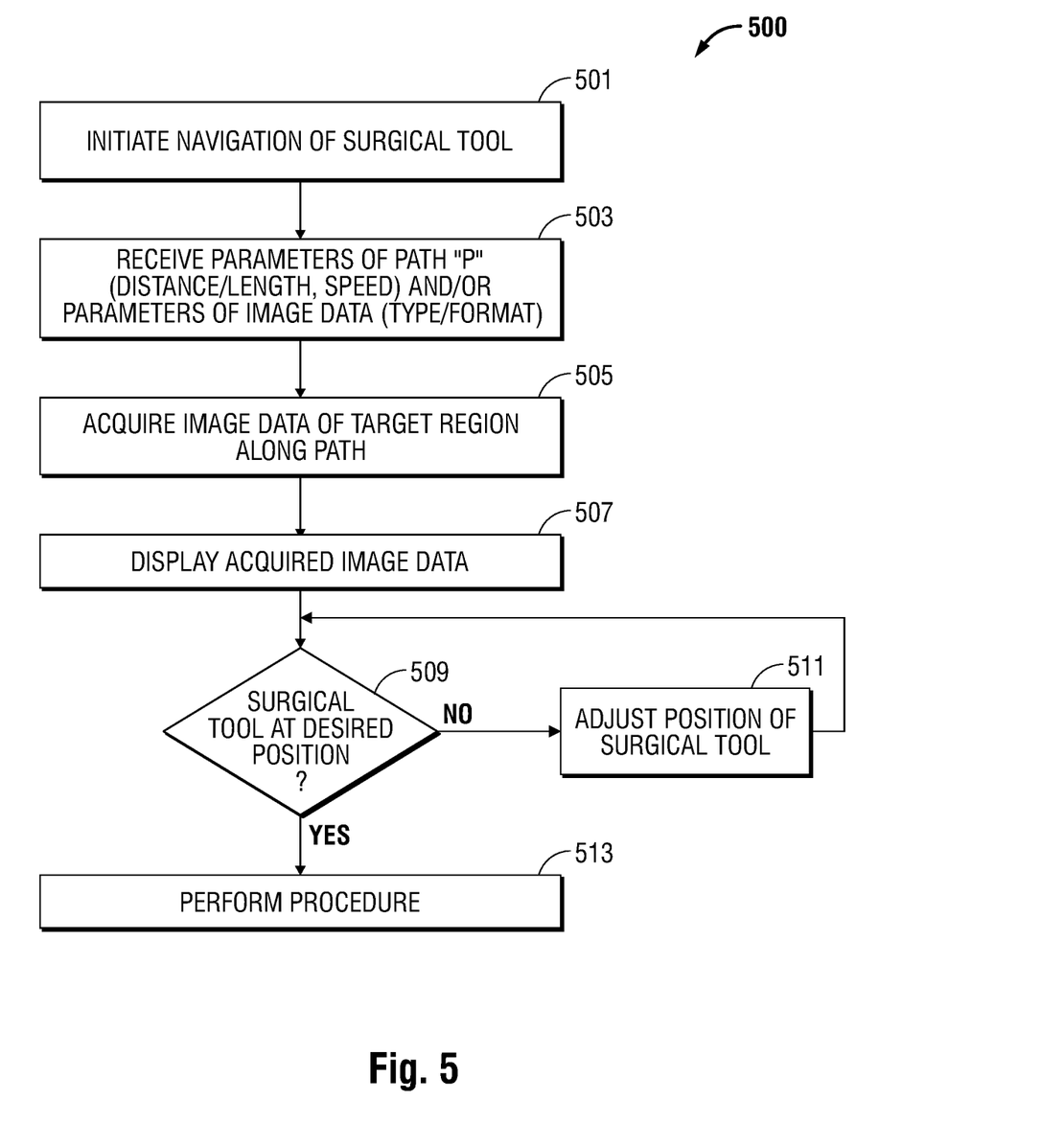
FIG. 5 is flow chart of an illustrative embodiment of a method for performing a navigation procedure to navigate a surgical tool to a target using the system of FIG. 1.

Having described the components of system 10 depicted in FIGS. 1-4, the following description of FIG. 5 provides an exemplary workflow of using the components of system 10, including the imaging device 140, to navigate to a target region (for example, through a luminal network of a patient or percutaneously through tissue) utilizing a previously generated navigation plan and the image data acquired by the imaging device 140. Although the methods illustrated and described herein are illustrated and described as being in a particular order and requiring particular steps, any of the methods may include some or all of the steps and may be implemented in any order not specifically described.

Turning now to FIG. 5, a method for navigating a surgical tool 130 to a target using the imaging device 140 of system 10, will now be illustrated and described as method 500. Method 500 begins at step 501 where navigation of a surgical tool 130 to a target region is initiated. Step 501 may include using a catheter guide assembly 200 (FIG. 2) using a navigation pathway previously planned, as described above. Alternatively, step 501 may include percutaneously inserting an ablation tool 300 (FIG. 3) to access the target region along a previously determined trajectory.

In step 503, computing device 100 receives parameters for the path "P" (FIG. 4) or parameters of the imaging device 140. In particular, in step 503 a user may input the distance or length of path "P" for which the imaging device 140 will traverse. Setting the length of path "P" sets the range of angular positions of the imaging device 140 relative to the target. Additionally, in step 503 a user may input the speed at which the imaging device 140 traverses along path "P." In one aspect, in step 503, a user may also input the type of image data desired to be acquired. For example, in certain instances a clinician may desire to generate a video stream of the target area. Alternatively, in certain instances the clinician may desire to expose the patient to less radiation and therefore may set the capture of the imaging device 140 to be run at a low frame rate or even be collimated to reduce radiation exposure. In one aspect, step 503 includes receiving a command for the imaging device 140 to acquire image data as a video along certain portions of path "P" and to acquire image data as an image or series of images along other portions of path "P." Step 503 may implemented at any point during method 500, such that modifications to the parameters of the path "P" and/or the parameters of the image device 140 may be made at any point during the navigation procedure.

In step 505, while traversing back and forth along path "P," imaging device 140 acquires image data of the target region. As described above, the image data acquired in step 505 may include a plurality of images of the target region captured along the path "P," a video of the target region captured along the path "P," combinations of images and video along the path "P," or images along portions of the path "P" and video along other portions of the path "P." Depending on the radiation output of the imaging device 140, it may be useful to reduce the level of radiation to which the patient is exposed by only capturing a series of images along the path "P" as opposed to capturing a continuous video of the target region along the path "P." The image data of the target region acquired in step 505 enables visualization of the target tissue located in the target region and the surgical tool 130 that is in the process of being navigated to the target tissue from multiple different perspectives.

In step 507, the image data acquired in step 505 is delivered to computing device 100 and displayed on display 110 for a clinician to view. Because the image data includes multiple images, or video, of the target region including the surgical tool 130 approaching the target tissue, the clinician is able to visualize the position of the surgical tool 130 with respect to the target tissue from multiple perspectives while simultaneously continuing to navigate the surgical tool 130 to the target tissue. This visualization of both the surgical tool 130 and the target, which is apparent in the images allows the clinician to overcome any navigation error or misplacement of the surgical tool 130 in the final centimeters or inches of navigation. At this point, the planned pathway to the target may be ignored and the final steps of the navigation can be undertaken under imaging utilizing the imaging device 140. Moreover, this imaging at different angles relative to the patient as the imaging device 140 traverses the path "P" provides for enhanced imaging of the position of the surgical tool 130 relative to the target at a number of angles. As noted above, as the clinician observes the images, either still or video, the effect is the impression of a three-dimensional-like image which is viewable by the clinician. As a result, the clinician is able to observe the relative position of the surgical tool 130 and the target from multiple perspective angles. Such a continuous multi-perspective visualization of the target region enables the clinician to interpolate the three-dimensional space and simultaneously navigate the surgical tool 130 to the target tissue without being required to repeatedly retract the surgical tool 130 and correct its trajectory.

In step 509, it is determined if the surgical tool 130 is at a desired location (for example, the target tissue or target region). In one aspect, step 509 is accomplished by determining whether a distance between a portion of the surgical tool 130 and an edge, or center, of the target tissue is within a predetermined threshold. For example, when the distance between the surgical tool 130 and the target tissue is more than the predetermined threshold, then it is determined that the surgical tool 130 is not at the desired position (no in step 509) and method 500 proceeds to step 511 where the clinician can adjust the position of the surgical tool 130. Specifically, in step 511, the clinician can continue to advance the surgical tool 130 while simultaneously visualizing the position of the surgical tool 130 relative to the target tissue from multiple angles with the image data being displayed on display 110. When the distance between the surgical tool 130 and the target tissue is less than the predetermined threshold, then it is determined that the surgical tool 130 is at the desired position (yes in step 509) and method 500 proceeds to step 513. In one aspect, the desired position is the center of the target tissue.

In step 513, the procedure is performed on the target tissue. As described above, method 500 may be used to navigate to a target region for various purposes. That is, step 513 may include any type of procedure, which may include for example, biopsy collection, marker placement, device placement, therapeutic treatments, agent delivery, ablation treatments including radiofrequency and microwave ablations, and any other such procedure that may benefit from enhanced and more accurate navigation to a target within a patient.

Figure 6:
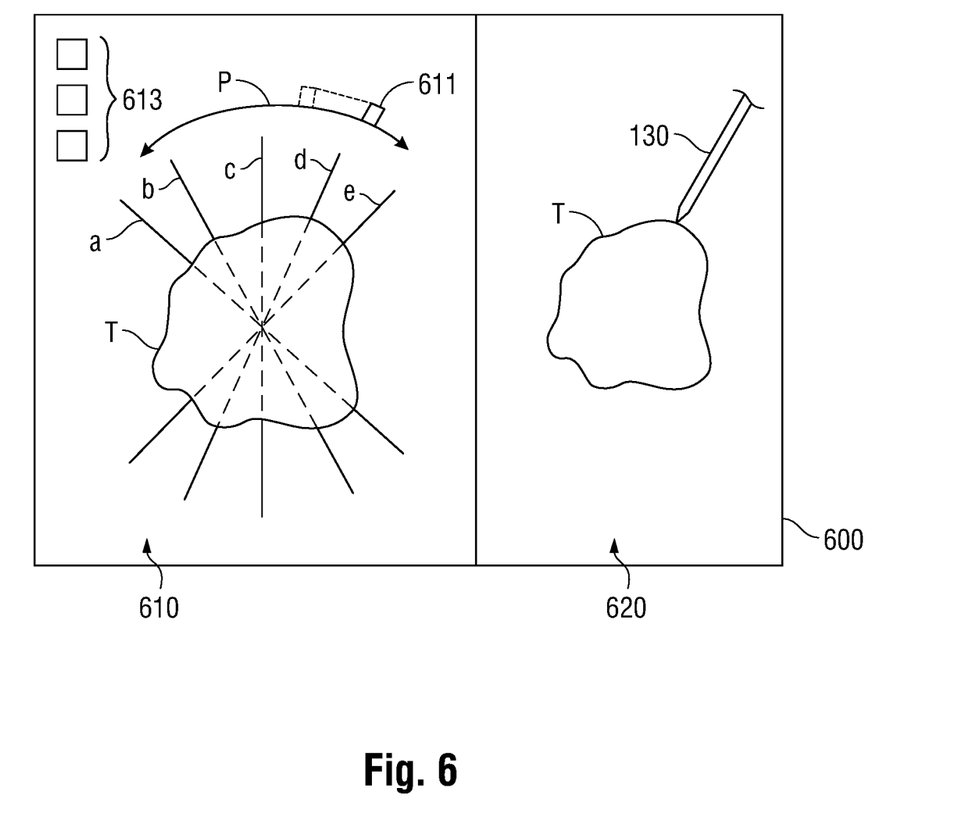
FIG. 6 is an example of a user interface displayable by the system of FIG. 1.

Turning now to FIG. 6, an example user interface 600 is illustrated which can be displayed on display 110 (FIG. 1). User interface 600 includes a split screen view which is presented to the user to assist the user in visualizing the position of the surgical tool 130 relative to the target from multiple perspectives while simultaneously advancing the surgical tool 130 to the target. Specifically, section 610 includes an axial slice of the target "T" which is generated from previously acquired CT image data. The particular axial slice of the target "T" displayed in section 610 corresponds to the axial position of the imaging device 140 relative to the patient. Icon 611 is a virtual representation of the position of the imaging device 140 at a given point in time. As the imaging device 140 traverses back and forth along the path "P," the position of icon 611 updates to represent the latest position of the imaging device 140. Section 611 also includes setting input region 613. Setting input region 613 may be used by an operator to input parameters associate with the imaging device 140 and path "P." As described above, a user may utilize input region 613 to set or modify the length of the path "P" (which in turn sets or modifies the angular range a-e of images to acquire), the speed at which the imaging device 140 traverses back and forth along the path "P," the image format to acquire, and the portions of the path "P" for which to capture different types of images formats. A graphical representation of the path "P" may also be included in section 610 and when the length of the path "P" is adjusted using region 613, the graphical representation is adjusted accordingly.

User interface 600 also includes section 620 which displays a continuous stream of images or video of the image data acquired by the imaging device 140. In particular, section 620 includes an image of target "T" and surgical tool 130 which continuously changes to a different perspective captured by the imaging device 140. Continuously displaying the target "T" and the position of the surgical tool 130 relative to the target "T" while simultaneously navigating the surgical tool enables the clinician to visualize the position of the surgical tool relative to the target "T" from multiple perspectives while still in the process of advancing the surgical tool 130 to the target "T." In this manner, as the clinician observes the display in section 620, the effect is the impression of a three-dimensional-like image which is being viewed by the clinician. As a result, the clinician is able to observe the relative position of the surgical tool 130 and the target from multiple perspective angles. Such a continuous multi-perspective visualization of the target region enables the clinician to interpolate the three-dimensional space and simultaneously navigate the surgical tool 130 to the target tissue without being required to repeatedly retract the surgical tool 130 and correct its trajectory.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A system for performing a navigation procedure, the system comprising:
   a surgical tool configured to be navigated to a target tissue located in a target area and to perform a surgical procedure on the target tissue;
   an imaging device configured to acquire image data of the target area while the surgical tool is being navigated to the target tissue, the imaging device including a motor configured to drive the imaging device in a first direction then a second direction opposing the first direction along an arcuate path relative to the target area;
   a user interface for a clinician to set one or more parameters of the imaging device, the parameters including at least one of a length of the path or a speed at which the imaging device traverses the path; and
   a computing device configured to receive the image data acquired by the imaging device and display the image data on the user interface in real-time as the imaging device drives in the first direction then the second direction opposing the first direction along the path, wherein the surgical tool can be navigated to the target tissue while under visualization of at least a portion of the surgical tool relative to the target tissue from multiple perspectives,
   wherein the imaging device is configured to output:
      a first level of radiation along a first portion of the path to acquire a plurality of fluoroscopic images along the first portion of the path, the first portion of the path having a first length; and
      a second level of radiation higher than the first level of radiation along a second portion of the path different from the first portion to acquire a video along the second portion of the path, the second portion of the path having a second length less than the first length.

2. The system for performing a navigation procedure of claim 1, wherein the surgical tool includes a catheter guide assembly configured to navigate to the target area via a natural orifice, the catheter guide assembly including a handle and an extended working channel extending from the handle and wherein at least one of a biopsy tool, a marker placement tool, a forceps, or an ablation tool is positionable within the extended working channel to access the target tissue.

3. The system for performing a navigation procedure of claim 1, wherein the surgical tool includes at least one of an ablation device including a tapered distal portion configured to percutaneously access the target tissue or a biopsy device including a tapered distal portion configured to percutaneously access the target tissue.

4. The system for performing a navigation procedure of claim 1, wherein the imaging device is configured to receive parameters controlling a format of the image data captured.

5. The system for performing a navigation procedure of claim 1, further comprising an electromagnetic field generator operably coupled to the computing device and configured to generate an electromagnetic field, the computing device configured to determine a location of the surgical tool based on the electromagnetic field.

6. A method for performing a navigation procedure comprising:
   initiating navigation of a surgical tool to a target tissue located in a target area;
   acquiring image data of the target area during navigation of the surgical tool to the target tissue by automatically traversing an imaging device back and forth along a path relative to the target area and acquiring the image data of the target area while traversing the path, wherein acquiring image data includes:
      outputting a first level of radiation along a first portion of the path to acquire a plurality of fluoroscopic images along the first portion of the path, the first portion of the path having a first length; and
      outputting a second level of radiation higher than the first level of radiation along a second portion of the path different from the first portion to acquire a video along the second portion of the path, the second portion of the path having a second length less than the first length;
   displaying the acquired image data in real-time as the imaging device traverses back and forth along the path during navigation of the surgical tool to the target tissue such that a position of the surgical tool relative to the target tissue is displayed real-time from multiple angles relative to the target area; and
   completing navigation of the surgical tool to the target tissue under visualization of the position of the surgical tool displayed in each of the multiple angles.

7. The method for performing a navigation procedure of claim 6, further comprising performing a procedure on the target tissue.

8. The method for performing a navigation procedure of claim 6, wherein initiating navigation of the surgical tool includes:
   initiating navigation of a catheter guide assembly including an extended working channel through a natural orifice; and
   inserting at least one of a biopsy tool, a marker placement tool, a forceps, or an ablation tool through the extended working channel.

9. The method for performing a navigation procedure of claim 6, wherein initiating navigation of the surgical tool includes percutaneously inserting at least one of an ablation tool or a biopsy tool including a tapered distal portion through tissue to access the target area.

10. The method for performing a navigation procedure of claim 6, further comprising receiving parameters controlling at least one of a format of the image data captured, a length of the path, or a speed at which the imaging device traverses the path.

11. The method for performing a navigation procedure of claim 6, further comprising:
generating an electromagnetic field about the target area; and
determining a location of the surgical tool based on the electromagnetic field.

12. The method for performing a navigation procedure of claim 6, further comprising determining that navigation of the surgical tool to the target tissue is complete.

13. The method for performing a navigation procedure of claim 12, wherein determining that navigation of the surgical tool to the target tissue is complete includes determining that a distance between the surgical tool and the target tissue in each of the multiple angles is below a threshold.

14. The method for performing a navigation procedure according to claim 6, wherein displaying the acquired image data during navigation of the surgical tool includes simultaneously displaying the position of the surgical tool relative to the target tissue from multiple angles relative to the target area and a corresponding position of the imaging device relative to the target area for each of the multiple angles.

15. A system for performing a navigation procedure, the system comprising:
an imaging device configured to acquire image data of a target area while a surgical tool is being navigated to a target tissue within the target area, the imaging device configured to move in a first direction then a second direction opposing the first direction along a path relative to the target area;
a user interface for a clinician to set one or more parameters of the imaging device, the parameters including at least one of a length of the path or a speed at which the imaging device traverses the path; and
a computing device configured to receive the image data acquired by the imaging device and display the image data on the user interface in real-time as the imaging device moves in the first direction then the second direction opposing the first direction along the path, wherein the surgical tool can be navigated to the target tissue while under real-time visualization of at least a portion of the surgical tool relative to the target tissue from multiple perspectives,
wherein the imaging device is configured to output:
a first level of radiation along a first portion of the path to acquire a plurality of fluoroscopic images along the first portion of the path, the first portion of the path having a first length; and
a second level of radiation higher than the first level of radiation along a second portion of the path different from the first portion to acquire a video along the second portion of the path, the second portion of the path having a second length less than the first length.

* * * * *